(12) United States Patent
Hilfrich

(10) Patent No.: US 9,568,480 B2
(45) Date of Patent: Feb. 14, 2017

(54) RAPID TEST FOR THE QUALITATIVE AND/OR QUANTITATIVE ANALYSIS OF ANTIBODIES AGAINST HUMAN PAPILLOMA VIRUSES (HPV) PRESENT IN BODY FLUID, AND DEVICE FOR CARRYING OUT THE RAPID TEST

(75) Inventor: Ralf Hilfrich, Huenfelden (DE)

(73) Assignee: Ralf Hilfrich, Huenfelden (DE)

( * ) Notice: Subject to any disclaimer, the term of this patent is extended or adjusted under 35 U.S.C. 154(b) by 0 days.

(21) Appl. No.: 13/989,804

(22) PCT Filed: Nov. 30, 2011

(86) PCT No.: PCT/DE2011/075292
§ 371 (c)(1),
(2), (4) Date: May 27, 2013

(87) PCT Pub. No.: WO2012/097788
PCT Pub. Date: Jul. 26, 2012

(65) Prior Publication Data
US 2013/0244228 A1    Sep. 19, 2013

(30) Foreign Application Priority Data
Dec. 3, 2010 (DE) .................. 10 2010 061 028

(51) Int. Cl.
*G01N 33/558* (2006.01)
*G01N 33/68* (2006.01)
*G01N 33/569* (2006.01)

(52) U.S. Cl.
CPC ........ *G01N 33/6854* (2013.01); *G01N 33/558* (2013.01); *G01N 33/56983* (2013.01); *G01N 2333/025* (2013.01)

(58) Field of Classification Search
None
See application file for complete search history.

(56) References Cited

U.S. PATENT DOCUMENTS

2008/0199851 A1    8/2008    Egan et al.

FOREIGN PATENT DOCUMENTS

| EP | 1271151 A1 | 1/2003 |
|---|---|---|
| WO | WO 97/02491 A1 | 1/1997 |
| WO | WO 98/23958 A1 | 6/1998 |

OTHER PUBLICATIONS

Paola Di Bonito. Serum antibody response to Human papillomavirus (HPV) infections detected by a novel ELISA technique based on denatured recombinant HPV16 L1, L2, E4, E6 and E7 proteins. Infectious Agents and Cancer, Nov. 2006, 1:6.*
Di Bonito et al. Serum antibody response to Human papillomavirus (HPV) infections detected by a novel ELISA technique based on denatured recombinant HPV16 L1, L2, E4, E6 and E7 proteins. Infect Agent Cancer. Nov. 8, 2006;1:6.*
Cui et al. A simple and rapid immunochromatographic strip test for detecting antibody to porcine reproductive and respiratory syndrome virus. J Virol Methods. Sep. 2008;152(1-2):38-42. Epub Jul. 10, 2008.*
Liu et al. Disposable electrochemical immunosensor diagnosis device based on nanoparticle probe and immunochromatographic strip. Anal Chem. Oct. 15, 2007;79(20):7644-53. Epub Sep. 19, 2007.*
Zarakolu et al. Preliminary Evaluation of an Immunochromatographic Strip Test for Specific Treponema pallidum Antibodies. Journal of Clinical Microbiology, Aug. 2002, vol. 40, p. 3064-3065.*
Christensen et al. Surface Conformational and Linear Epitopes on HPV-16 and HPV-18 L1 Virus-like Particles as Defined by Monoclonal Antibodies. Virology 223, 174-184 (1996).*
Kirnbaueret al. A virus-like particle enzyme-linked immunosorbent assay detects serum antibodies in a majority of women infected with human papillomavirus type 16. J Natl Cancer Inst. Apr. 6, 1994;86(7):494-9.*
Karem et al. Optimization of a Human Papillomavirus-Specific Enzyme-Linked Immunosorbent Assay. Clin Diagn Lab Immunol. May 2002; 9(3): 577-582.*
Peng et al. Comparison of a new gold-immunochromatographic assay for the detection of antibodies against avian influenza virus with hemagglutination inhibition and agar gel immunodiffusion assays. Vet Immunol Immunopathol. May 15, 2007;117(1-2):17-25. Epub Feb. 12, 2007.*
MyBioSource: "HPV16L1 antigen", XP002672343, Retrieved from the Internet: URL:http://www.mybiosource.com/datasheet.php?products_id=318636, [retrieved on Mar. 26, 2012], Dec. 2006.
Luan Yi, et al., "Comparison of Detection Antibodies to Human papillomaviruses 16 L1 in the Cervical Cancer People with Different Recombinant Antigen", Virologica Sinica, vol. 17 (4), pp. 308-311, Nov. 2002.
David Opalka, et al., "Simultaneous quantitation of antibodies to neutralizing epitopes on virus-like particles for human papillomavirus types 6, 11, 16, and 18 by a multiplexed luminex assay", Clinical and Diagnostic Laboratory Immunology, vol. 1, No. 1, pp. 108-115, Jan. 2003.
D. Skiba, "Prognostic Significance of Serum Antibodies to HPV-16 L1 Virus-like Particles in Patients with Invasive Cervical Cancer", Anticancer Research, vol. 26, pp. 4921-4926, Dec. 2006.

* cited by examiner

*Primary Examiner* — Nick Zou
(74) *Attorney, Agent, or Firm* — Leydig, Voit & Mayer, Ltd.

(57) ABSTRACT

A rapid test for a qualitative and/or quantitative assay of antibodies present in body fluid against human papilloma viruses (HPV) includes mixing a specimen of body fluid with a reagent which essentially comprises a predetermined quantity of physiologically acting liquid and a predetermined quantity of at least one HPV-specific antigen. The mixture is fed to an analysis which utilizes a change that is at least one of measurable or perceivable by a user.

3 Claims, 3 Drawing Sheets

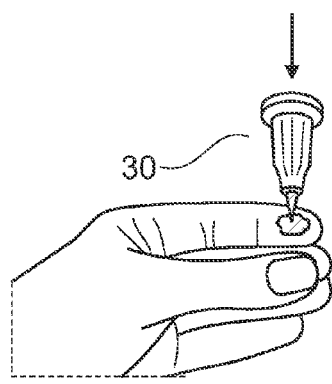
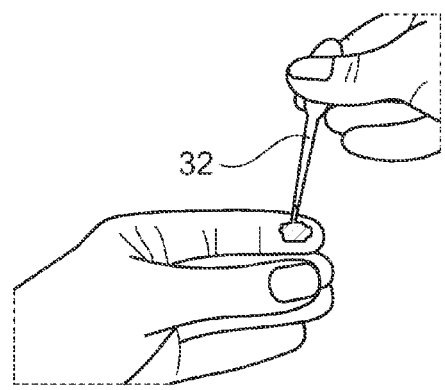
Fig. 5A Fig. 5B
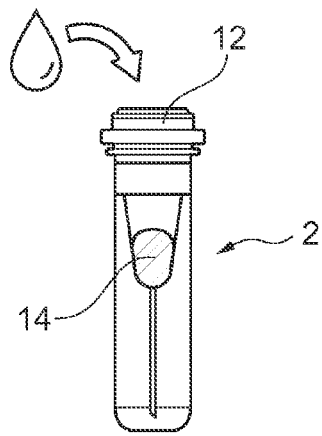
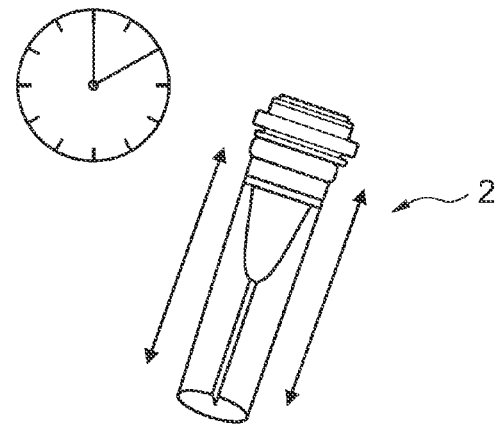
Fig. 5C Fig. 5D
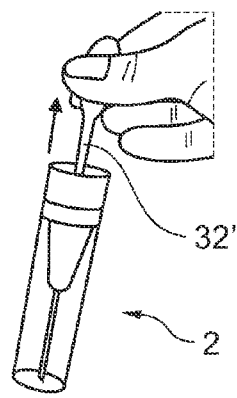
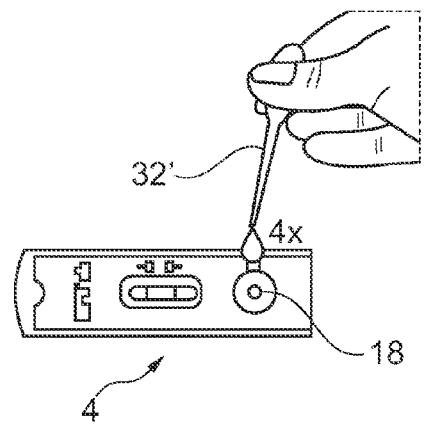
Fig. 5E Fig. 5F

RAPID TEST FOR THE QUALITATIVE AND/OR QUANTITATIVE ANALYSIS OF ANTIBODIES AGAINST HUMAN PAPILLOMA VIRUSES (HPV) PRESENT IN BODY FLUID, AND DEVICE FOR CARRYING OUT THE RAPID TEST

CROSS REFERENCE TO RELATED APPLICATIONS

This application is a U.S. National Phase application under 35 U.S.C. §371 of International Application No. PCT/DE2011/075292, filed on Nov. 30, 2011, and claims benefit to German Patent Application No. DE 10 2010 061 028.3, filed on Dec. 3, 2010. The International Application was published in German on Jul. 26, 2012, as WO 2012/097788 A1 under PCT Article 21 (2).

FIELD

The invention relates to a rapid test for the qualitative and/or quantitative assay of antibodies present in body fluid against human papilloma viruses. The invention furthermore relates to a device for carrying out such a rapid test.

BACKGROUND

Human papilloma viruses, abbreviated to HPV, form a group of viruses which have meanwhile been classified into more than 100 types. The viruses attack the epithelial cells of the skin or various mucous membranes and cause an uncontrolled tumorous growth in the infected cells. The tumours are usually benign and lead merely to the formation of warts on the affected area of skin or mucous membrane on which the infection with the viruses is present.

However, human papilloma viruses not only cause benign tumours. Some HPV types can also cause malignant changes. For example, human papilloma viruses are suspected of being involved in the development of cancer of the neck of the uterus, so-called cervical cancer. Human papilloma viruses are also suspected of causing carcinomas of the vagina, penis and anus, or at least of being involved in the development thereof.

In order to prevent such tumorous growth, in recent years vaccines against human papilloma viruses have been developed, and have been approved in Germany. By the vaccination, the probability of infection of the vaccinated person by human papilloma viruses is reduced considerably. However, the vaccination is only effective if the person subsequently also shows antibodies against human papilloma viruses and the antibodies are present in an appropriate concentration. In this respect, proof of the efficacy of the vaccination is significantly important.

However, a commercially available detection system for HPV antibodies in body fluids has not so far existed.

SUMMARY

In an embodiment, the present invention provides a rapid test for a qualitative and/or quantitative assay of antibodies present in body fluid against human papilloma viruses (HPV) that includes mixing a specimen of body fluid with a reagent which essentially comprises a predetermined quantity of physiologically acting liquid and a predetermined quantity of at least one HPV-specific antigen. The mixture is fed to an analysis which utilizes a change that is at least one of measurable or perceivable by a user.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

The figures show:

FIG. 4 shows the analysis system according to FIG. 2 after carrying out a rapid test for the qualitative and/or quantitative assay of antibodies present in body fluid against human papilloma viruses with a positive result and FIG. 5A to 5F show method steps in carrying out a rapid test for the qualitative and/or quantitative assay of antibodies present in body fluid against human papilloma viruses.

DETAILED DESCRIPTION

Figure 1:
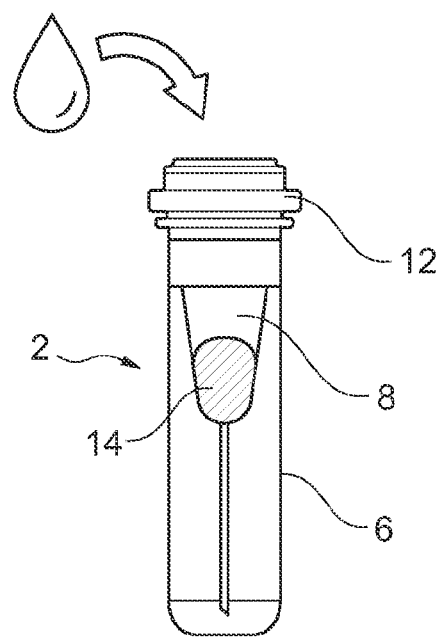
FIG. 1 shows a side view of a possible embodiment of a receptacle of a device for carrying out a rapid test for the qualitative and/or quantitative assay of antibodies present in body fluid against human papilloma viruses.

An aspect of the present invention is to provide a rapid test for the qualitative and/or quantitative assay of antibodies present in body fluid against human papilloma viruses having the abovementioned features. A device for carrying out such a rapid test is furthermore to be proposed.

A rapid test according to the invention for the qualitative and/or quantitative assay of antibodies against human papilloma viruses, also called HPV in the course of the invention, present in body fluid provides that in a first method step a specimen of body fluid, in particular a specimen of body fluid taken from a human, is mixed with a reagent, wherein the reagent essentially comprises a predetermined quantity of physiologically acting liquid, such as, for example, a saline solution, and a predetermined quantity of at least one HPV-specific antigen. In a second method step the mixture of the reagent and the specimen of body fluid is then fed to an analysis which utilizes a change which is measurable and/or can be perceived by a user.

As a result of the rapid test according to the invention, a detection of antibodies against HPV can be provided in a simple manner and with little outlay. An expensive and complicated analysis in a central laboratory is not necessary. In the rapid test according to the invention, the diagnostic investigation can already be carried out on site, that is to say in the practice of a registered doctor or directly on the ward in a hospital.

In order to be able to carry out an analysis for the detection of human antibodies against HPV, according to the invention the analysis is preceded by a method step in which the specimen of body fluid taken from a human is brought together with the at least one HPV-specific antigen so that a complex of the antigen and any antibodies present in the sample is already formed before the analysis. If the antibodies associated with the at least one antigen are present in the sample, the reagent is inactivated. If no corresponding antibodies are present in the specimen, the reagent remains reactive. This reactive property of the reagent is then utilized in the analysis.

It has been found that a dwell time of the specimen of body fluid in the reagent of about 10 minutes is sufficient for the reagent to be inactivated or not, depending on whether or not antibodies are present in the specimen. As a result, the entire rapid test can be carried out in a very short time, so that, for example, reliable results are available within a period of time of less than one hour after the specimen has been taken.

In the rapid test according to the invention, it is important that the HPV-specific antigen is held in the reagent without the HPV-specific antigen losing its ability to react with antibodies against HPV or decreasing in its reactivity with respect to the antibodies. In the rapid test according to the invention, the physiologically acting liquid is therefore used, which liquid, on the basis of its physiological mode of action, neither in the short term nor in the long term has a negative influence on the HPV-specific antigen or the mode of action thereof with respect to antibodies against HPV. In this context, short term is to be understood as meaning a period of time of up to about 4 to 5 weeks. Long term furthermore is to be understood as meaning a period of time of up to about 2 to 3 years.

TRIS-BSA having a pH of from about 7.0 to about 9.0, preferably 7.2 to 7.4, can be employed, for example, as the physiologically acting liquid. In this context, TRIS is the abbreviation for tris(hydroxymethyl)aminomethane and BSA is the abbreviation for bovine serum albumin. Such a physiologically acting liquid is particularly stable, so that a negative influence on the HPV-specific antigen is permanently avoided.

It is also conceivable to employ a saline solution, in particular having a pH of from about 7.0 to about 9.0, preferably 7.2 to 7.4, as the physiologically acting liquid.

Depending on whether or not antibodies against human papilloma viruses are present in the specimen of body fluid, a change which is measurable and/or can be perceived by a user occurs in the course of the analysis or such a change remains absent. In the rapid test according to the invention, it is thus discovered by the analysis by measurement or perception by a user whether the antibodies associated with the at least one antigen are present in the specimen or lie above the detection limit of the method or are not present or lie below the detection limit of the method.

Since the rapid test according to the invention merely requires taking a specimen of body fluid, which is then fed to a reagent, and the mixture of reagent and specimen being subsequently subjected to an analysis, a result can already be provided with a few simple interventions from taking the specimen through to getting the test result. The results of the investigation are also promptly available. The rapid test according to the invention is therefore particularly suitable for checking the efficacy of a vaccination against HPV, for example in the practice of the vaccinating doctor.

The change in the course of the analysis, which change can be perceived by the user, can be a visual, acoustic and/or tactile change. For example, at least one fluorescent medium can be used. The analysis can utilize a staining effect or discolouring effect or a colour reaction. In principle, the analysis can utilize any type of measurable reaction. The analytical result can be rapidly determined by all of these possibilities.

The rapid test according to the invention is suitable for the detection of antibodies against human papilloma viruses. Such viruses are infective on humans. In principle, the rapid test according to the invention can also be employed for the detection of antibodies against non-human papilloma viruses which, for example, infect animals. In this case a correspondingly different antigen is to be used in the course of the rapid test.

Preferably, in the event of an absence of HPV antibodies in the specimen or a quantity of HPV antibodies in the specimen which lies below or in the region of a predetermined detection limit for the HPV-specific antigen, a medium is changed in a manner which can be perceived by a user and/or measurably. The change can take place over a predetermined section of the surface of the medium or over a predetermined volume of the medium.

A predetermined quantity of the mixture of the reagent and the specimen of body fluid should be fed to the analysis. Preferably, the predetermined quantity should be a part quantity of the mixture present. As a result, several diagnostic investigations can be carried out from one specimen taken and the reagent combined with this, for example in order to acquire a statistical confirmation of the result.

The quantity of the at least one HPV-specific antigen can furthermore be determined by a predetermined detection limit for the quantity to be determined of the at least one HPV antibody present in the fluid specimen. The detection limit is preferably the particular detection limit desired, for example in order to ascertain that a certain quantity of antibodies against HPV is present in the fluid specimen in order thus to confirm the immunity, for example on the basis of a successful vaccination.

Furthermore, at least one type of antibodies against HPV present in the specimen can be determined qualitatively by the choice of the at least one HPV-specific antigen employed. For example, it can be determined by an appropriate choice of the antigen whether antibodies against human papilloma viruses, in particular of the type 16, are present in the specimen. In this case an HPV16-specific antigen is employed in the rapid test.

It can also be determined by an appropriate choice of the antigen whether antibodies against human papilloma viruses with the L1 protein are present in the specimen, for example this can be the L1 protein of the HPV of type 16. In this case an HPV16L1-specific antigen is employed in the rapid test. In principle, antigens can be employed which identify antibodies against the L1 protein of HPV and also of types other than type 16.

In the course of the invention, HPV16 is to be understood as meaning that this is type 16 of human papilloma viruses. Furthermore, in the course of the invention HPV16L1 is to be understood as meaning that this is the protein of human papilloma viruses of type 16 called L1. In the course of the invention, the antigen employed concerns virus constituents which can trigger an immune response.

According to a further aspect, the invention relates to a device for carrying out a rapid test for the qualitative and/or quantitative assay of antibodies present in body fluid against human papilloma viruses.

The device according to the invention can be employed for a rapid test of the type described above.

The device for carrying out a rapid test for the qualitative and/or quantitative assay of antibodies present in body fluid against human papilloma viruses comprises a receptacle in which a reagent essentially of a predetermined quantity of a physiologically acting liquid, such as, for example, saline solution, and a predetermined quantity of at least one HPV-specific antigen is present, wherein body fluid from a patient's specimen can be introduced into the reagent in the receptacle.

The device furthermore comprises an analysis system which utilizes a change which is measurable and/or can be perceived by a user. For example, the analysis system can utilize a staining effect or discolouring effect or a colour reaction. The analysis system is furthermore configured for accommodating a predetermined quantity of a substrate present in the receptacle.

The device according to the invention as a result is simple in construction and renders possible a diagnostic investigation of the patient's specimen already on site, for example at the site where the specimen is taken, with a low outlay. The determination of antibodies present in body fluid against human papilloma viruses is therefore already possible in the practice of a registered doctor or in the hospital directly on the ward. An involved and expensive analysis in a central laboratory is not necessary. As a result of this there is already a time advantage in an investigation carried out with the device according to the invention.

Since the analysis system can utilize a staining effect or a colour reaction, commercially available and particularly inexpensive test strips, for example, in cassette form, can be made use of. In order to be able to employ such an analysis system, in the device according to the invention the at least one HPV-specific antigen which binds to the antibodies can be held in the receptacle. The physiologically acting liquid in the receptacle serves to keep the antigen intact and thus to render possible the use of the device with such a biological component for a predetermined period of time. Any drying of the liquid, for example, would destroy the antigen.

Any desired antigen which binds to antibodies against papilloma viruses can be used as the antigen. If antibodies against human papilloma viruses of type 16, in particular type 16L1, are to be detected, corresponding HPV16-specific antigens or HPV16L1-specific antigens are to be employed. In this context, aggregated antigens are preferably used.

The device according to the invention renders possible a diagnostic investigation with a specimen in which any type of body fluid is present. For example, blood, in particular whole blood, serum, plasma, saliva and secretion can be used as the body fluid.

It is expedient for the receptacle to be separate. As a result, the receptacle forms a separate unit with respect to the analysis system, which in turn represents a separate unit. The receptacle can thereby be used separately and independently of the analysis system.

It is furthermore expedient for the receptacle to be closable. For this, the receptacle can have a lid which, for example, can be screwed on to the receptacle by means of a thread. Since the receptacle can be closed off, the reagent and/or the specimen of body fluid can be introduced in a simple manner. Due to the closing of the receptacle, leak-proof storage and handling of the receptacle is rendered possible. For example, in the closed state of the receptacle, mixing of the patient's specimen and the reagent can be achieved particularly readily by the closed receptacle being shaken back and forth by a user.

It is furthermore expedient for the receptacle and, where appropriate, a lid or a covering cap to be made of plastic. As a result, the receptacle is particularly inexpensive to produce.

According to one embodiment of the invention, the receptacle can comprise an inner vessel and a housing surrounding the inner vessel. The inner vessel can be cylindrical or conical in construction. Due to the housing, the receptacle can be handled readily, in particular grasped readily. The housing also offers protection on the inner vessel against external influences.

According to a further embodiment, the receptacle can have a sampling device or receiving device for the patient's specimen, in particular a capillary sampling device or receiving device. As a result, for example, a quantity of blood can already be accommodated by means of the receptacle itself via the sampling device or capillary sampling device in a simple manner and guided into the inner space in which the reagent is present.

The rapid test from the taking of the specimen through to the combining and mixing with the reagent in which the antigen is present can therefore be carried out particularly easily and with particularly little outlay.

One embodiment of the invention provides that the analysis system contains a conjugate which essentially comprises a predetermined quantity of at least one HPV-specific molecule and/or human-specific molecule and a substance which gives a reaction which is measurable and/or can be perceived by a user. For example, the substance can cause a colour reaction or result in staining in the event of spatial accumulation.

Due to the substance, coloured labelling of the components to be determined is possible. Due to the HPV-specific molecule, a reaction with an associated HPV-specific antigen which is still reactive takes place, so that, as a result, via the presence of the reactive HPV-specific antigen a colour detection takes place in the course of the diagnostic investigation.

The HPV-specific molecule of the conjugate can be an HPV16-specific molecule, in particular an HPV16L1-specific molecule. Such a molecule can be an antibody. It is furthermore conceivable that the HPV-specific molecule is a cell molecule of the human cell which functions as a receptor. It is important that the molecule reacts with the virus content of the substrate from the receptacle, that is to say the HPV reagent, if this content is still reactive. The reaction causes binding of the molecule to free binding sites of the HPV reagent or of the antigen.

The human-specific molecule of the conjugate reacts with a still reactive human-specific component of the substrate from the receptacle. The human-specific molecule is a molecule which is directed against the human-specific content of the substrate. The molecule can be directed, for example, against the human HPV antibody in the patient's specimen which forms a constituent of the substrate.

The substance used for the labelling preferably comprises colloidal gold and/or silver. In this context, the gold particles or silver particles of the substance preferably have a diameter of from about 2 nm (nanometer) to about 100 nm (nanometer). Preferably, the colloidal gold or silver is present in aggregated form.

According to a further embodiment of the invention, the analysis system contains a carrier medium onto or into which the quantity of substrate from the receptacle can flow in the direction of at least one three-dimensional axis, preferably starting from a filling point. As a result, the path travelled by the substrate on the carrier medium can be utilized to give at least one colour signal at least at one predetermined point of the path. Classification according to different colour signals is thereby possible.

It is expedient for the carrier medium to be a porous medium, in particular a porous membrane. As a result, flowing of the substrate in the direction of the at least one three-dimensional axis is promoted.

It is furthermore expedient for a medium which generates the flow of the substrate to be provided. The medium can be at the end of the flow path of the substrate. The medium can be formed by the carrier medium itself, for example if the carrier medium is a porous membrane. The medium can then be formed in several layers by a section of the carrier medium, so that in this region the carrier medium has a higher absorption effect than in the at least one other section which is formed by fewer layers or strata and therefore has lower absorption properties.

The carrier medium and/or medium for generating the flow can be formed by a foam mat, blotting paper or absorbent paper or a combination thereof.

According to a further embodiment of the invention, the analysis system contains a predetermined quantity of at least one molecule which is fixed on a predetermined first point or a predetermined first region of the carrier medium and in the event of reactive reagent being in the receptacle binds to the antigen. As a result, those molecules of the substrate which react with the conjugate and therefore form a compound with the conjugate are held. In this context, the at least one molecule fixed on the carrier medium acts as a trapping molecule, so that the components of the substrate which have reacted with the conjugate are held on the predetermined first region or the first point.

Alternatively or in addition, a further embodiment of the invention provides that the analysis system contains a predetermined quantity of at least one molecule which is fixed on a predetermined first point or a predetermined first region of the carrier medium and in the event of reactive human HPV antibodies being in the substrate in the receptacle binds to the human antibodies. As a result, the human content obtained from the patient's specimen, in particular the HPV content of the substrate, is used in order to conduct the detection by the analysis system.

It is expedient for the at least one molecule which is fixed on the carrier medium and the at least one molecule which forms the conjugate to be identical to one another. Molecules which are different from one another can of course also be employed. In this context it is important that the two molecules, both the trapping molecule and the conjugate molecule, undergo binding to the corresponding content of the substrate, that is to say the human content or the virus content.

A further embodiment of the invention provides that the analysis system contains a predetermined quantity of at least one molecule which binds to at least one constituent of the conjugate and which is fixed on a predetermined second point or a predetermined second region of the carrier medium, the second point or the second region being arranged downstream of the first point when viewed in the direction of flow of the substrate introduced. As a result, it can be checked whether the substrate introduced on to the carrier medium or into the carrier medium has flowed up to the second point or the second region. If a colour signal takes place at the second region or the second point, it is thus confirmed that the substrate at least with its components bonded to the conjugate also actually passes the first point or the first region and therefore the quantity of substrate introduced into the analysis system was sufficient.

According to a further aspect, the invention includes a receptacle of the type described above.

The invention also includes an analysis system of the type described above.

The invention renders it possible for reliable test results already to be available within less than one hour after a specimen of body fluid has been taken. It has been found, in fact, that after a few minutes of the specimen of body fluid being fed to the reagent with the HPV-specific antigen the required reaction of the mixture already occurs, and the analysis of the mixture can therefore already be carried out after this short time. If test strips are used for the analysis, it has been found that the rapid test can be carried out within from 15 to about 25 minutes from taking of the specimen and a reliable result is then already available.

Embodiment Example

Further aims, advantages, features and possible uses of the present invention emerge from the following description of an embodiment example with the aid of the drawings. In this context, all the features described and/or shown on the figures by themselves or in any desired appropriate combination form the subject matter of the present invention, also independently of their combination in the claims or references back to them.

Figure 2:
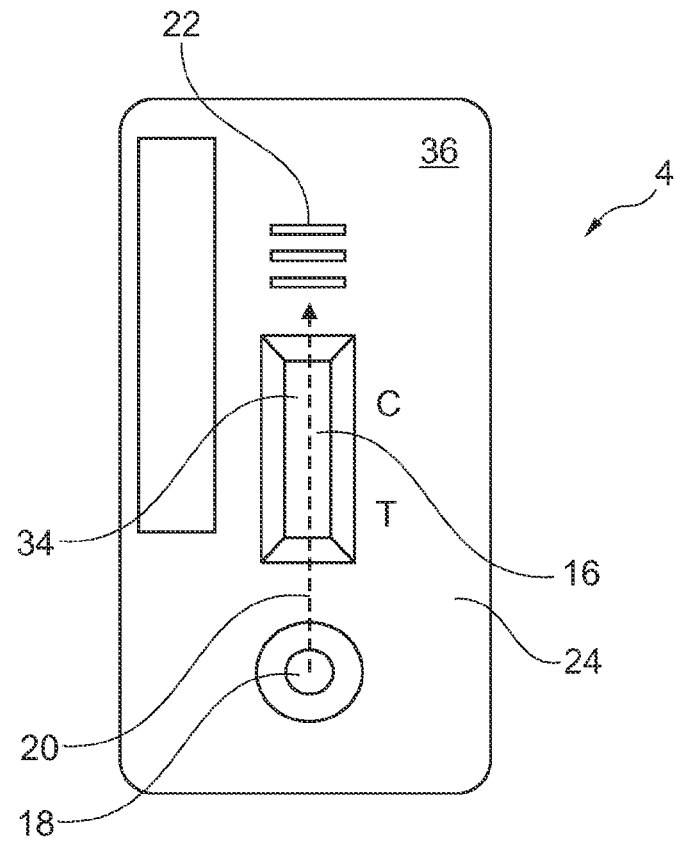
FIG. 2 shows a plan view of a possible embodiment of an analysis system of a device for carrying out a rapid test for the qualitative and/or quantitative assay of antibodies present in body fluid against human papilloma viruses.

FIGS. 1 and 2 show—in diagram form—a possible embodiment of a device for carrying out a rapid test for the qualitative and/or quantitative assay of antibodies present in body fluid against human papilloma viruses, which comprises at least a receptacle 2 (FIG. 1) and an analysis system 4 (FIG. 2). The device makes it possible to carry out the rapid test on specimens of any desired body fluid, such as, for example, whole blood, serum, plasma, saliva and secretion.

By means of the device, human antibodies present in the specimen against HPV of any desired type and in principle also of any desired concentration can be determined. For simplicity, the following statements relate by way of example to the embodiment of the device by means of which antibodies of type 16L1 present in the specimen can be detected. The embodiment described in the following is furthermore configured such that, in the event of a positive analytical result, such a high concentration of HPV16L1 antibodies is present in the patient's specimen that the person from whom the specimen has been taken is reliably immunized against human papilloma viruses.

The receptacle 2 contains in its inside a reagent 14 which essentially comprises a predetermined quantity of physiologically acting liquid, such as, for example, a saline solution, and a predetermined quantity of an HPV16L1-specific antigen. The receptacle 2 is preferably constructed in the nature of a tube, the outer circumference of which forms a housing 6. The housing 6 surrounds an inner vessel 8, in which the reagent 14 is present. The inner vessel 8 can be conical in construction.

The receptacle 2 furthermore has a covering cap 12, which can preferably be attached, in particular screwed on, to an opening of the receptacle 2. Body fluid from the patient's specimen can of course also be fed to the inside of the receptacle 2 in which the reagent 14 is present via the opening of the receptacle 2 which can be covered by the covering cap 12.

The inside of the receptacle 2 or the inner vessel 8 forms an essentially leak-proof inner space which is essentially leak-proof even when the receptacle 2 is shaken.

The analysis system 4 performs the diagnostic investigation by utilizing a staining effect or a discolouring effect. Due to the analysis system 4 an analytical result is thus promptly available and the analysis can already be carried out on site in the practice of the doctor carrying out the treatment or in the hospital directly on the ward.

The analysis system 4 has a filling point 18 into which a predetermined quantity of substrate to be analysed can be introduced. In this context, the amount of substrate which can be introduced is predetermined by the depth and preferably the diameter of the edge of the opening or the circumferential wall of the filling point 18.

The filling point 18 is formed, for example, by a opening through a lid part 36 of a housing 24. In addition to the lid part 36, the housing 24 has a base part (not visible in FIG. 2), a carrier medium 16 which is preferably formed from a porous material, in particular a porous membrane, being arranged between the base part and the lid part 36.

The lid part 36 and the base part (not visible) can be formed against one another so that the housing is constructed as one part. The lid part 36 and the base part (not visible) can of course be at least two separate parts.

The carrier medium 16 or the porous membrane is elongated in construction and projects at least in part beyond the opening of the filling point 18, so that a substrate introduced or dripped into the filling point 18 can flow in the direction according to the arrow 20. Flowing of the substrate is caused by a medium 22 which is particularly absorbent and thereby generates a flow of the substrate in the direction according to the arrow 20. In the embodiment of the analysis system 4 according to FIG. 2, the medium 22 is formed by sections of the carrier medium 16 laid on one another in several layers, as a result of which the carrier medium has a higher absorbency in this region than in the region of fewer layers, in particular one layer, which is constructed between the filling point 18 and the medium 22.

The analysis system 4 furthermore contains a conjugate (not visible in FIG. 2) which essentially comprises a predetermined quantity of an HPV16L1-specific molecule which is labelled with colloidal gold.

Preferably, the conjugate (not visible in FIG. 2) is arranged close to or in the region of the filling point 18 on the carrier medium 16, so that when the analysis system 4 is filled via the filling point 18 the substrate bonds directly with the conjugate.

The analysis system 4 furthermore contains a predetermined quantity of a molecule (not visible in FIG. 2) which is fixed on a predetermined first region on the carrier medium 16. The first region (not visible in FIG. 2), when viewed in the direction of flow 20, is arranged approximately in the region of the marking T provided on the lid part 36.

The analysis system 4 furthermore contains a predetermined quantity of a molecule (not visible in FIG. 2) which is fixed on a predetermined second region on the carrier medium 16. The second region, when viewed in the direction of flow 20, is arranged approximately in the region of the marking C provided on the lid part 36 and is thus downstream of the first region.

The amount of the molecule (not visible in FIG. 2) fixed in the first region has the property, in the case of a reactive substrate which flows in the direction of flow 20 and reaches the first region, of bonding with a constituent of the substrate. The molecule therefore has a trapping action with respect to the still reactive substrate, which in the case of binding via the conjugate accumulates in the first region.

The predetermined quantity of the at least one other molecule is preferably likewise specific for the conjugate, so that when the substrate flowing in the direction of the arrow 20, together with the conjugate, reaches the second region it is bound by the fixed molecules present there and an accumulation of the conjugate thus also occurs at this second region.

Because of the labelling of the conjugate with colloidal gold, the accumulation in the first region and the second region in each case causes a visible discolouration on the carrier medium 16. So that this discolouration can also be perceived visually by the user of the analysis system 4, the lid part 36 has an opening which forms a viewing field 34 via which the user can look at the carrier medium 16.

Figure 3:
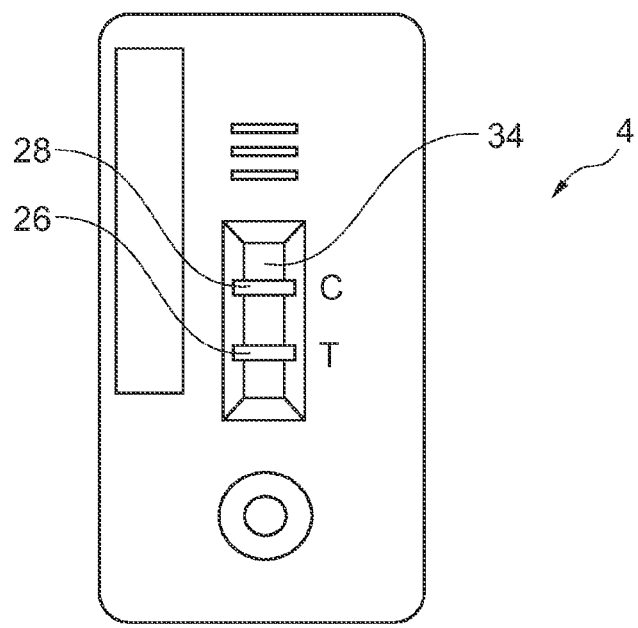
FIG. 3 shows the analysis system according to FIG. 2 after carrying out a rapid test for the qualitative and/or quantitative assay of antibodies present in body fluid against human papilloma viruses with a negative result.

FIG. 3 shows the analysis system 4 after a rapid test has been carried out with a patient's specimen in which no human antibodies against HPV16L1 are present. As can be seen from this, a discoloured line is in each case visible in the viewing field 34 in the first region 26 and in the second region 28.

Since no antibodies against HPV16L1 are present in the patient's specimen which has been taken, the reagent of the receptacle 2 has remained reactive when mixed with the patient's specimen. As a result, the substrate removed from the receptacle 2 from the patient's specimen and the reagent is also still reactive with respect to the analysis system 4. In this case the substrate thus binds to the conjugate on the carrier medium 16. The complex thereby formed has been bound by the quantity of molecules in the first region 26 and held on the carrier medium 16 in the first region 26 by the quantity of the one molecule fixed there, so that due to the colloidal gold in the conjugate a visual discolouration has taken place in the first region 26.

The complex from the substrate, at least the conjugate, has flowed further in the direction according to the arrow 20 up to the second region 28. The quantity of the at least one other molecule, which quantity is fixed in the second region 28 on the carrier medium 16, has also trapped the complex and therefore the colloidal gold in the second region 28 and because of the accumulation of the colloidal gold has led to a visual discolouration in the second region 28.

Due to the discolouration of the first region 26 it is demonstrated that no antibodies against HPV16L1 or merely antibodies below the detection limit are present in the patient's specimen. It is furthermore confirmed by the discolouration in the second region 28 that the substrate and conjugate have flowed into the second region 28 and therefore the quantity of specimen introduced into the filling point 18 was sufficient for the analysis.

Figure 4:
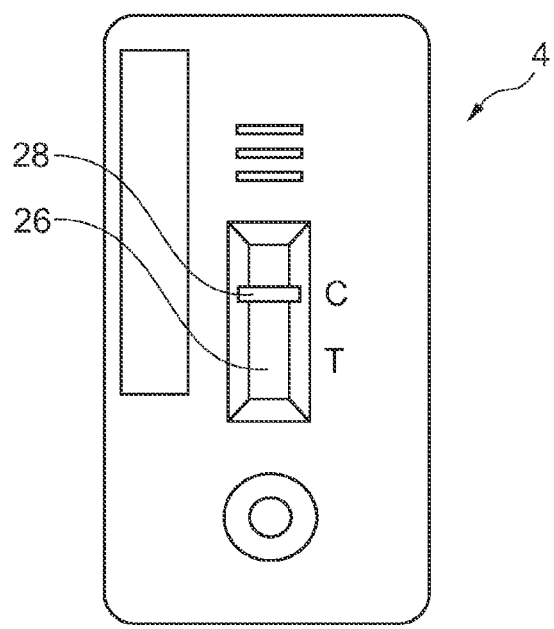

FIG. 4 shows the result of a rapid test with a patient's specimen in which human antibodies against HPV16L1 are present in a quantity lying above the detection limit of the analysis system 4. A discolouration has remained absent in the first region 26. In contrast, the second region 28 shows a discolouration, so that proper introduction of a sufficient quantity of substrate into the filling point 18 is thereby confirmed. The absence of discolouration in the first region 26 is to be attributed to the fact that the reagent 14 present in the receptacle 2 has been inactivated by the HPV16L1 antibodies present in the patient's specimen. As a result, a reaction of the substrate with the conjugate has not taken place in the analysis system 4, so that a colour signal is absent in the first region 26.

FIGS. 5A to 5F show the method steps in carrying out a rapid test for the qualitative or quantitative assay of antibodies present in body fluid against human papilloma viruses, in which assay the receptacle 2 and the analysis system 4 are employed.

A specimen of whole blood is taken. For this, for example, the finger can be pricked by means of a lancet and a predetermined amount of blood can be taken up therefrom by means of a pipette 32 (FIGS. 5A and 5B). A predetermined amount of the blood is then fed to the receptacle 2 with the reagent 14 and the receptacle 2 is shaken several times and left to stand over a predetermined period of time, for example 10 minutes. Mixing of the quantity of specimen with the reagent 14 has thereby taken place (FIG. 5D).

In a further step, the substrate now present in the receptacle 2 is at least partly removed by means of a pipe 32' and a predetermined quantity, for example one or more drops of the substrate, is fed to the analysis system 4 via the filling point 18. Depending on whether or not a quantity of antibodies against HPV16L1 lying above the detection limit of the analysis system 4 is present in the patient's specimen, a discolouration occurs in the first region 26 or such a discolouration remains absent (FIG. 5F).

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B." Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise.

LIST OF REFERENCE SYMBOLS

2 Receptacle
4 Analysis system
6 Housing
8 Inner vessel
12 Covering cap
14 Reagent
16 Carrier medium
18 Filling point
20 Direction of flow
22 Medium
24 Housing
26 First region
28 Second region
30 Lancet
32, 32' Pipette
34 Viewing field
36 Lid part

The invention claimed is:

1. A device for carrying out a rapid test for at least one of a qualitative or quantitative assay of antibodies present in body fluid against human papilloma virus type 16 (HPV16), the device comprising:
   (a) a receptacle in which a reagent essentially comprising a predetermined quantity of physiologically acting liquid and a predetermined quantity of at least one antigen is present, the receptacle being further configured to receive body fluid from a patient's specimen so as to introduce the body fluid into the reagent in the receptacle,
   wherein the antigen is aggregated and reactive to antibodies present in the body fluid that are specific against HPV16L1 protein (HPV16L1-specific antibodies), and wherein the liquid acts on the antigen to maintain reactivity of the antigen with respect to the antibodies, and
   (b) an analysis system which (i) is configured for accommodation of a predetermined quantity of a substrate containing the reagent and the body fluid present in the receptacle and (ii) utilizes a change that is effected by the substrate that is at least one of measurable or perceivable by a user,
   wherein the analysis system contains
   (1) a conjugate which essentially comprises a predetermined quantity of at least one molecule and a substance which causes a reaction which is at least one of measurable or perceivable by a user or in the event of spatial accumulation results in a change which is at least one of measurable or perceivable by a user,
   wherein the molecule of the conjugate is specific against HPV16 LI protein and binds to the antigen when the antigen is reactive with respect to the molecule of the conjugate,
   (2) a carrier medium onto or into which the applied quantity of substrate from the receptacle can flow in the direction of at least one three-dimensional axis, and
   (3) a predetermined quantity of at least one trapping molecule which is fixed on a predetermined first point or a predetermined first region of the carrier medium and binds to the antigen when the antigen is reactive with respect to the trapping molecule,
   wherein the trapping molecule and the molecule of the conjugate are identical to one another in such a way that both undergo binding to the antigen when the antigen is reactive with respect to the HPV16L1-specific antibodies.

2. The device according to claim 1, wherein the receptacle is closeable.

3. The device according to claim 1, wherein the substance comprises at least one of colloidal gold or colloidal silver.

* * * * *